US012685744B2

(12) United States Patent
Maddi et al.

(10) Patent No.: US 12,685,744 B2
(45) Date of Patent: Jul. 21, 2026

(54) ANTI-FUNGAL COMPOSITIONS AND METHODS FOR USING SAME

(71) Applicant: The Research Foundation for The State University of New York, Amherst, NY (US)

(72) Inventors: Abhiram Maddi, Tonawanda, NY (US); Stephen J. Free, Williamsville, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 828 days.

(21) Appl. No.: 17/777,001

(22) PCT Filed: Nov. 16, 2020

(86) PCT No.: PCT/US2020/060697
§ 371 (c)(1),
(2) Date: May 13, 2022

(87) PCT Pub. No.: WO2021/097411
PCT Pub. Date: May 20, 2021

(65) Prior Publication Data

US 2022/0409651 A1 Dec. 29, 2022

Related U.S. Application Data

(60) Provisional application No. 62/936,160, filed on Nov. 15, 2019.

(51) Int. Cl.

| | |
|---|---|
| ***A61K 31/7048*** | (2006.01) |
| ***A61K 9/00*** | (2006.01) |
| ***A61K 9/06*** | (2006.01) |
| ***A61K 33/06*** | (2006.01) |
| ***A61K 33/14*** | (2006.01) |
| ***A61P 31/00*** | (2006.01) |

(52) U.S. Cl.
CPC ........ *A61K 31/7048* (2013.01); *A61K 9/0014* (2013.01); *A61K 9/06* (2013.01); *A61K 33/06* (2013.01); *A61K 33/14* (2013.01); *A61P 31/00* (2018.01)

(58) Field of Classification Search
CPC .... A61K 31/7048; A61K 9/0014; A61K 9/06; A61K 33/06; A61K 33/14; A61P 31/00
See application file for complete search history.

(56) References Cited

U.S. PATENT DOCUMENTS 8,188,085 B2 * 5/2012 Greenlee ................ A61K 31/41 514/252.05

FOREIGN PATENT DOCUMENTS

JP 2007070264 A 3/2007
KR 20110069303 A 6/2011

OTHER PUBLICATIONS

Belz. Chem. Commun., 2017, 53, 9238 (Year: 2017).*
Wojtczak. Glossary of Medical Education Terms. (Year: 2002).*
Maouni. African Journal of Biotechnology vol. 6 (11), pp. 1289-1292. (Year: 2007).*
Ao. Eukaryotic Cell. vol. 14. pp 792-803. (Year: 2015).*
Li et al. Frontiers in Cellular and Infection Microbiology. vol. 8, Article 286 (Year: 2018).*
Segal et al. Clinical Infectious Diseases. 2007:44 (Year: 2007).*
Belz, T., et al., An atypical interaction explains the high-affinity of a non-hydrolyzable S-linked 1,6-α-mannanase inhibitor, Chem. Commun., 2017, vol. 53, pp. 9238-9241.
Thompson, A.J., et al., Evidence for a Boat Conformation at the Transition State of GH76 α-1,6-Mannanases—Key Enzymes in Bacterial and Fungal Mannoprotein Metabolism, Angewandte Chemi, Mar. 15, 2015, vol. 54, No. 18, pp. 5378-5382.
Fernandes, P.Z., Design and Synthesis of Substrates and Inhibitors for Mechanistic Insights into alpha-Mannoidases and alpha-L-Rhamnosidases, Doctoral Thesis, University of Melbourne, Apr. 2018, 184 pages.
Pubchem CID No. 143207115, 5-[[(4R,5R,6S)-4,5-dihydroxyoxazinan-6-yl]methyldisulfanyl]-2-nitrobenzoic acid, Dec. 7, 2019, 8 pages.
Ao, J., et al., The N-linked outer chain mannans and the Dfg5p and Dcw1p endo-α-1,6-mannanases are needed for the incorporation of Candida albicans glycoproteins into the cell wall, Eukaryotic Cell, Jun. 5, 2015, vol. 14, No. 8, 792-803.
Mancuso, R., et al., Functions of Candida albicans cell wall glycosidases Dfg5p and Dcw1p in biofilm formation and HOG MAPK pathway, PeerJ, Sep. 28, 2018, 23 pages.
Boumaaza, B., et al., Effects of Two Salts Compounds on Mycelial Growth, Sporulation, and Spore Germination of Six Isolates of Botrytis cinerea in the Western North of Algeria, International Journal of Microbiology, Mar. 26, 2015, vol. 2015, 8 pages.
Ma, W., et al., Recent studies on the biological production of D-mannose, Applied Microbiology and Biotechnology, Oct. 22, 2019, vol. 103, pp. 8753-8761.
Chavan Shrawan R. et al. “Iminosugars spiro-linked with morpholine-fused 1, 2, 3-triazole: Synthesis, conformational analysis, glycosidase inhibitory activity, antifungal assay, and docking studies”, ACS Omega, 2017, pp. 7203-7218, vol. 2, No. 10.

(Continued)

*Primary Examiner* — Scarlett Y Goon
*Assistant Examiner* — Samantha Lynn Schachermeyer
(74) *Attorney, Agent, or Firm* — Hodgson Russ LLP

(57) ABSTRACT

Provided are compounds, compositions, and methods for treatment of fungal infections. The compositions comprise the mannose disaccharide analog (2R,3S,4S,5S,6R)-2-((((3S,4R,5R)-4,5-dihydroxypiperidin-3-yl)methyl)thio)-6-(hydroxymethyl)tetrahydro-2H-pyran-3,4,5-triol. Methods are also provided for the treatment of fungal infections comprising contacting the infected site with a therapeutically effective concentration of the present compound or compositions.

11 Claims, 13 Drawing Sheets

(56) References Cited

OTHER PUBLICATIONS

Juvvadi Praveen R. et al. "Calcineurin in fungal virulence and drug resistance: Prospects for harnessing targeted inhibition of calcineurin for an antifungal therapeutic approach", Virulence, 2017, pp. 186-197, vol. 8, No. 2.

Liu Xin et al. "Antifungal compounds against Candida infections from traditional Chinese medicine", BioMed Research International, 2017, pp. 1-12, vol. 4614183.

* cited by examiner

ManSIFG

Chemical Formula: $C_{12}H_{23}NO_7S$

Molecular Weight: 325.38

A

D-Mannose

B

ANTI-FUNGAL COMPOSITIONS AND METHODS FOR USING SAME

CROSS-REFERENCE TO RELATED APPLICATIONS

This application is a national stage application of PCT/US2020/060697, filed Nov. 16, 2020, which claims priority to U.S. Provisional patent application No. 62/936,160, filed on Nov. 15, 2019, the disclosures of which are incorporated herein by reference.

BACKGROUND OF THE INVENTION

Fungal infections pose a growing problem, particularly amongst the immunocompromised individuals. About a 100 million people in the USA and close to a billion people in the world get fungal infections on an annual basis. Systemic candidiasis has a high mortality rate of 40-60%.

*Candida albicans* is the cause of majority of the human fungal infections. *Candida albicans*, an opportunistic fungal pathogen causes oral and systemic candidiasis. Candidal infection may range from mild, superficial mucosal involvement seen in most patients, to fatal, disseminated disease in severely immunocompromised patients. The conditions that can result in candidiasis include prolonged antibiotic treatment, immunosuppressive conditions that arise due to genetic disorders or drug therapy, HIV infection, medical and dental prostheses, and dry mouth. Oral mucosal candidiasis occurs in millions of people worldwide. Vaginal candidiasis occurs in a majority of women at least once in their lifetime with a significant rate of recurrence. Candidemia resulting from the invasion of *C. albicans* into the bloodstream in human patients occurs in patients in intensive care. This is problematic as candidemia has an alarming mortality rate of 35-67% and is associated with extremely high treatment costs. Candidemia leading to disseminated candidiasis also occurs in preterm neonates resulting in significant impairment of neurodevelopment. As such, *candida* infections have a significant impact on public health and healthcare costs. Furthermore, the clinical incidence of oral candidiasis is very high in cancer patients, with a majority of infections being attributed to *Candida albicans*. The risk of systemic/invasive candidiasis is also increased in immunocompromised patients and may eventually become life-threatening.

While the number of cases of infections caused by fungal organisms continues to increase, a rapid emergence of antifungal drug resistance among *Candida* species has been reported, particularly in recurrent infections. Moreover, given the toxicity concerns relating to currently anti-fungal agents, there continues to be a need for development of novel therapeutic compositions with reduced toxicity.

SUMMARY OF THE DISCLOSURE

The present disclosure provides compounds, compositions, and methods for the treatment of fungal infections. The compound is a mannose disaccharide analog. Compositions comprising the mannose disaccharide analogs and methods for using the compound and the composition are also disclosed. The mannose disaccharide analog may be used alone or in combination with a calcium salt, such as $CaCl_2$). The compound and compositions may be used for local application at or about the site of fungal infection or may be administered to the individual via any route of administration regionally or systemically.

In an aspect, this disclosure provides a mannose disaccharide analog. In an embodiment, the mannose disaccharide analog is (2R,3S,4S,5S,6R)-2-((((3S,4R,5R)-4,5-dihydroxypiperidin-3-yl)methyl)thio)-6-(hydroxymethyl) tetrahydro-2H-pyran-3,4,5-triol, ($C_{12}H_{23}NO_7S$ (Mol. wt. 325.38) and is termed herein as Mannose sulphur isofagomine, MannoseSIFG or ManSIFG. The disclosure also provides compositions, such as pharmaceutical compositions, comprising or consisting essentially of, ManSIFG, and optionally, $CaCl_2$).

In an aspect, this disclosure provides methods for treatment of fungal infections comprising contacting the site of fungal infection with a composition comprising ManSIFG.

DESCRIPTION OF THE DISCLOSURE

Every numerical range given throughout this specification includes its upper and lower values, as well as every value and every narrower numerical range that falls within it, as if such value or narrower numerical ranges were all expressly written herein.

The terms "a" or "an" are intended to include the singular as well as the plural of the particular item being reference. Any reference to a singular includes its plural and vice-versa.

This disclosure provides compounds, compositions, and methods for treatment of fungal infections. The compositions comprise or consist essentially of, a sugar polymer, which is a mannose disaccharide analog, represented by the following formula.

Formula 1

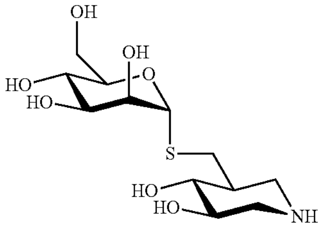

Although this formula is drawn in the α conformation, both α and β diastereomers are encompassed by the presented disclosure.

This compound, (2R,3 S,4S,5S,6R)-2-((((3 S,4R,5R)-4,5-dihydroxypiperidin-3-yl)methyl)thio)-6-(hydroxymethyl) tetrahydro-2H-pyran-3,4,5-triol, ($C_{12}H_{23}NO_7S$ (Mol. wt. 325.38) is termed herein as Mannose sulphur isofagomine, MannoseSIFG, or ManSIFG. The present compounds also include α and β diastereomers and/or pharmaceutically acceptable salts thereof. Any trisaccharides and/or polysaccharides of this molecule can be also used.

Figure 1:
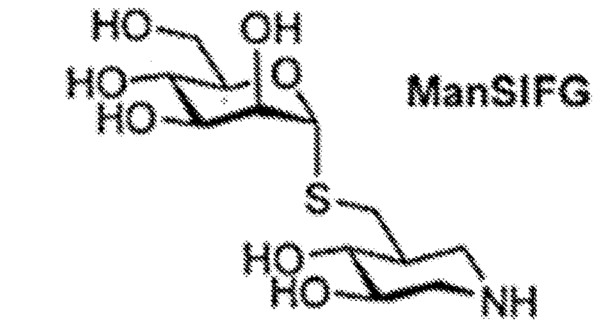
FIG. 1 is a representation of the structure of a mannose disaccharide analog.

In an aspect, this disclosure provides a mannose disaccharide represented by Formula 1 above and in FIG. 1, termed herein as MannoseSIFG (used interchangeably with ManSIFG).

In an aspect, this disclosure provides compositions comprising or consisting essentially of MannoseSIFG. MannoseSIFG may be the only disaccharide present in the composition. MannoseSIFG may be the only di- or poly-saccharide present in the composition. The composition may be free of one or more of the following: any monosaccharide, any disaccharides other than MannoseSIFG, and any polysaccharides.

In an aspect, this disclosure provides a method for the treatment of fungal infections. The method comprises administering to an individual in need of treatment a composition comprising a therapeutically effective amount of MannoseSIFG. Administration of the anti-fungal agent may be locally (e.g., topically) or regionally (e.g., oral cavity) or systemically (e.g., via oral, i.v., i.p., i.m. administrations). Anti-fungal agents in general can be used at dosages known in the art. For example, in general a dosage of 0.1 microgram to 1 gram per kg may be used. MannoseSIFG may be used at a concentration from 0.25 micrograms/ml to 500 micrograms/ml, or 0.5 μg/ml to 500 μg/ml. In an embodiment, the concentration of MannoseSIFG is from 0.25 to 250 micrograms/ml. In embodiments, the concentration of Mannose SIFG may be 0.5 μg/ml to 250 μg/ml, 0.25 μg/ml to 200 μg/ml, 1 μg/ml to 200 μg/ml, 25 μg/ml to 100 μg/ml, 60 μg/ml to 70 μg/ml and so on. While not intending to be bound by any particular theory, it is considered that ManSIFG may interfere with the cross-linking of cell wall proteins in the wall by presenting as an analog to N-linked mannan, a structure that is critical for covalent incorporation of cell wall proteins.

In an embodiment, the present disclosure provides a method of treating fungal infections of the oral cavity, comprising providing to the oral cavity of the individual in need of treatment a therapeutically effective amount of the compound or compositions of the present disclosure. The oral compositions may comprise ManSIFG alone or with $CaCl_2$).

The effective amount of the compounds or compositions described herein, or pharmaceutically acceptable salts or prodrugs thereof, may be determined by one of ordinary skill in the art. In general the dosage amounts of ManSIFG may be from about 0.05 to about 100 mg/kg of body weight of ManSIFG per day, which may be administered in a single dose or in the form of individual divided doses, such as from 1 to 4 times per day. In embodiments, the dosage amount can be from about 0.05 to about 75 mg/kg of body weight of ManSIFG per day, about 0.5 to about 50 mg/kg of body weight of ManSIFG per day, about 0.5 to about 25 mg/kg of body weight of ManSIFG per day, about 1 to about 20 mg/kg of body weight of ManSIFG per day, about 1 to about 10 mg/kg of body weight of ManSIFG per day. The particular dosage and frequency may be varied depending upon a variety of factors, including the species, age, body weight, general health, gender, severity of the particular condition and other health conditions of the individual.

In embodiments, the method comprises administering to an individual in need of treatment, MannoseSIFG and a calcium salt. The calcium salt may be $CaCl_2$). Any calcium salt that can regulate chitin synthesis in fungi via the calcium-calcineurin pathway can be used. Such salts include calcium phosphate, calcium carbonate, calcium acetate, calcium gluconate, calcium lactate, calcium gluceptate, calcium glycerophosphate. The calcium salt may be present from 5 mg/ml to 120 mg/ml. A concentration of 100 mg/ml when given i.v. is considered safe in humans. If by oral administration about 1-2 gm can be given daily or 0.8 mEq by i.m. (intramuscular) can be given 1-4 times/week for healthy adults. For i.v. administration a 2-10% calcium chloride can be administered at 2-14 mEq every 3 days. (See drugs.com/monograph/calcium-salts for more details).

In an embodiment, the dosage can be about 0.05 to about 100 mg/kg of body weight of ManSIFG per day, which may be administered in a single dose or in the form of individual divided doses, such as from 1 to 4 times per day, and 1-2 gm Ca salt, such as $CaCl_2$), given daily or 0.8 mEq which may be administered in a single dose or in the form of individual divided doses, such as from 1 to 4 times per day. In embodiments, the dosage amount of ManSIFG can be from 0.05 to 75 mg/kg, 0.5 to 50 mg/kg, 1 to 20 mg/kg or 1 to 10 mg/kg of body weight of ManSIFG per day, and 0.8 mEq of $CaCl_2$) per day or the $CaCl_2$) may be 2-14 mEq per 3 days.

The anti-fungal agents can be administered in a therapeutically effective amount. The term "therapeutically effective amount" as used herein refers to an amount of an agent sufficient to achieve, in single or multiple doses, the intended purpose of treatment. Treatment does not have to lead to complete cure, although it may. Treatment can mean alleviation of one or more of the symptoms or markers of the indication. The exact amount desired or required will vary depending on the particular compound or composition used, its mode of administration, patient specifics, and the like. Appropriate effective amount can be determined by one of ordinary skill in the art informed by the instant disclosure using only routine experimentation. Within the meaning of the disclosure, "treatment" also includes treatment of relapse, or prophylaxis as well as the alleviation of acute or chronic signs, symptoms and/or malfunctions associated with the indication. Treatment can be orientated symptomatically, for example, to suppress symptoms. It can be effected over a short period, over a medium term, or can be a long-term treatment, such as, for example within the context of a maintenance therapy.

The anti-fungal agents can be administered in a pharmaceutical carrier as pharmaceutical compositions. The pharmaceutical compositions may be in the form of solids, powders, solutions, suspensions, emulsions, gels, pastes, solid or in any other physical form. Compositions may be dissolved or suspended in a solvent immediately before use, or used as is. The administrable compositions may be prepared by dissolving, suspending, or emulsifying one or more of the active ingredients in a diluent. Examples of diluents are distilled water for injection, physiological saline, physiologic buffer, vegetable oil, alcohol, and a combination thereof. Further, the compositions may contain stabilizers, solubilizers, suspending agents, emulsifiers, soothing agents, buffers, preservatives, etc. The pharmaceutical compositions may be formulated into a sterile solid or powdered preparation, for example, by freeze-drying, and may be used after sterilized or dissolved in sterile injectable water or other sterile diluent(s) immediately before use. The compositions can include one or more standard pharmaceutically acceptable carriers. Some examples herein of pharmaceutically acceptable carriers can be found in *Remington: The Science and Practice of Pharmacy* (2013) 22nd Edition, Pharmaceutical Press. Oral compositions may comprise additives such as excipients carriers. Such additives can be liquids, such as water and oils, saline, glucose or the like, and auxiliary, stabilizing, thickening, or lubricating agents, wetting or emulsifying agents, or pH buffering agents, gelling or viscosity enhancing additives, detergents and solubilizing agents (e.g., TWEEN® 20, TWEEN® 80 also referred to as polysorbate 20 or 80), anti-oxidants (e.g., ascorbic acid, sodium metabisulfite), preservatives (e.g., Thimersol, benzyl alcohol), bulking substances (e.g., lactose, mannitol), flavoring agents, colors, and the like, depending upon the route of administration and the preparation desired. See *Remington: The Science and Practice of Pharmacy* (2013) 22nd Edition, Pharmaceutical Press. Non-aqueous solvents or vehicles can be used such as propylene glycol, polyethylene glycol, vegetable oils, such as olive oil and corn oil, gelatin, and injectable organic esters such as ethyl oleate.

The formulations may be lyophilized and redissolved or resuspended just before use. The formulation may be sterilized by, for example, filtration through a bacteria retaining filter, by incorporating sterilizing agents into the compositions, by irradiating the compositions, or by heating the compositions. The pharmaceutical composition may be administered via any route that is appropriate, including but not limited to mucosal, oral, parenteral, sublingual, transdermal, rectal, transmucosal, topical, via inhalation, via buccal administration, or combinations thereof. Parenteral administration includes, but is not limited to, intravenous, intraarterial, intraperitoneal, subcutaneous, intramuscular, intrathecal, and intraarticular. The agents(s) can also be administered in the form of an implant, which allows a slow release of the compound(s), as well as a slow controlled i.v. infusion. If administered orally, the anti-fungal agent compositions can be in the form of a tablet, capsule, pill, powder, paste, granules, elixir, solution, suspension, dispersion, gel, syrup, oral rinse, mucosal patch or any other ingestible form. In embodiments, the present anti-fungal compound may be introduced via intramuscular, intravenous, intraperitoneal, intradermal, mucosal, submucosal, or subcutaneous routes.

The compositions may contact an infected area of the individual, either externally, or internally. The compositions may be applied by topical application as a drop, spray, gel or ointment to the mucosal epithelium of the eye, nose, mouth, anus, or vagina, or onto the epidermis of the outer skin at any part of the body. Additional or alternative routes of application can be by spray, aerosol, or powder application through inhalation via the respiratory tract. The compositions may be delivered via the oral/GI route by combining with the food, feed or drinking water e.g. as a powder, a liquid, or tablet, or by administration directly into the mouth as liquid, gel, tablet, or capsule, or to the anus as a suppository. The present compositions may be incorporated into articles that come in contact with the skin or mucosal epithelium, such as bandages, braces, wrappings, diapers, clothing, pads, or any other similar articles.

The anti-fungal agent compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated.

The individual in need of treatment may be any animal, including human and non-human animals. Non-human animals include all vertebrates, e.g., mammals and non-mammals, such as non-human primates, sheep, dogs, cats, cows, horses, chickens, amphibians, and reptiles. The subject may also be livestock such as, cattle, swine, sheep, poultry, and horses, or pets, such as dogs and cats. The individual may be immunocompromised.

The methods of the disclosure described herein can be employed for individuals of any species, gender, age, ethnic population, or genotype. Accordingly, the term individual (used interchangeably with "subject") includes males and females, and it includes elderly, elderly-to-adult transition age subjects, adults, adult-to-pre-adult transition age subjects, and pre-adults, including adolescents, children, and infants.

The present compounds or compositions may be used in dermatological applications, oral applications, including oral rinses, toothpastes and other materials in contact with teeth (e.g., flossing materials), denture cleaning and lining materials, oral administration materials, i.v. administrations materials, and in combination therapy. The present compounds and compositions may be used for human use or for veterinary or agricultural applications.

Examples of fungal infections treatable by the methods described herein include infections caused by the genus *Candida* or the genus *Aspergillus* or the genus *Trychophoton*. Examples of the *Candida* species include *Candida albicans, Candida guilliermondii, Candida glabrata, Candida parapsilois, Candida apicola, Candida tropicalis, Candida lustaniae*, and *Candida krusei*. Examples of the *Trychophoton* genus include *Trychophoton rubrum, Trychophoton mentagrophytes, Trychophoton verrucosum* and *Trychophoton tonsurans*. Examples of conditions that involve fungal infections include any type of candidiasis. Further examples include invasive candidiasis, candidemia, oesophageal candidiasis, oral thrush, vaginal thrush, denture stomatitis, diaper rash, fungal infections of the skin and cutaneous tissues, athlete's foot, onychomycosis etc.

The methods and compounds or compositions as described herein may be used for both prophylactic and therapeutic treatment of fungal infections. For prophylactic use, a therapeutically effective amount of the compounds or compositions described herein are administered to a subject prior to exposure (e.g., to an individual who may be at risk of contracting a fungal infection), during a period of potential exposure to fungal infections, or after a period of potential exposure to fungal infections. An example of an individual at risk of contracting a fungal infection is immune compromised individual.

The methods and compounds or compositions as described herein may be used for treatment of routine fungal infections, which will need over the counter medication or prescription antifungal medication in outpatient or hospital setting.

The compounds and compositions of the present disclosure may be combined with other anti-fungal agents or with other anti-microbial agents in the prophylaxis or treatment of various infections.

The following examples are provided as illustrative examples and are not intended to be restrictive in any way.

Example 1

These examples describe the effects of ManSIFG on *C. albicans*.

ManSIFG Inhibits Growth of *C. albicans*

The wildtype *C. albicans* strain SC5314 was cultured from frozen stock in Yeast Nitrogen Base (YNB) media with 2% glucose and grown overnight at 30° C. with shaking at 225 rpm as described previously (Chinnici et al., 2019). Cell concentration of the overnight culture was determined by hemocytometer. This was used to inoculate fresh cultures with a final starting concentration of $5\times10^5$ cells/ml in fresh YNB contain either no treatment (control) or various concentrations (31.25, 62.5, or 125 µg/ml) of the mannose disaccharide inhibitor. The cultures were run in duplicates and incubated at 30° C. on a nutator. Cell concentration was analyzed by counting on hemocytometer at 10, 14, 18, and 24-hour time points. Statistical analysis was done using two-tailed Student's t-Test.

Figure 2:
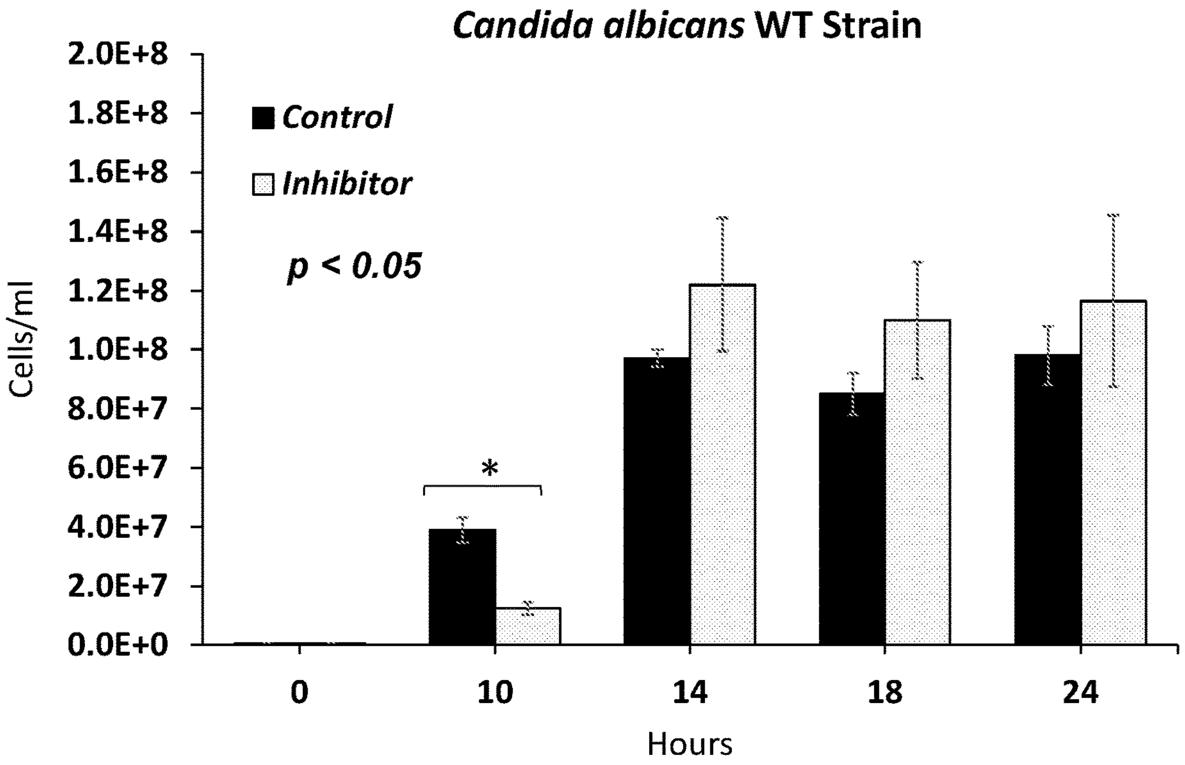
FIG. 2 is a representation of the effect of ManSIFG on the growth of *Candida albicans*. The number of *C. albicans* cells/ml in the presence or absence of ManSIFg are shown at various times of exposure.

Data shows that growth of *C. albicans* wild type was inhibited by ManSIFG (62.5 µg/ml) significantly at 10 hours as compared to control cultures (FIG. 2). However, at later time points there was no significant difference between control and inhibitor cultures. The reason for this could be that ManSIFG molecule could have been processed by the *Candida* cells and thus a new dosage of the molecule will be needed for a sustained anti-*candida* effect. A similar effect is commonly seen in antibiotics. As such, more frequent application or administration of the present compounds or compositions may be carried out.

ManSIFG Inhibits Hyphal Growth of *C. albicans*

The formation of hyphae is required for invasion of tissue and pathogenesis of mucosal candidiasis. Furthermore, hypha formation is also a virulence determinant (Chaffin et al., 2008, Cullen & Edgerton, 2016). The initial stage of hyphal formation begins with germ tube formation from a yeast cell. This germ tube then elongates to become a full-fledged hypha or mycelium. The *C. albicans* strain SC5314 (Wild Type) was cultured from frozen stock in Yeast Nitrogen Base (YNB) media with 2% glucose and grown overnight at 30° C. with shaking at 225 rpm. Cell concentration was determined by hemocytometer. The overnight culture was used to inoculate fresh YNB supplemented with or without 20% Fetal Bovine Serum (FBS) with a starting cell concentration of $5\times10^5$ cells/ml in a total volume of 500 µl in small sterile tubes. The addition of FBS induces the formation of germ tubes and growth of hyphal cells. ManSIFG (62.5 µg/ml) was added to test cultures but not to control cultures. The experiment was done in triplicates for test and control cultures. The culture tubes were placed on a nutator inside a 37° C. incubator and grown for 24 hours. Germ tubes were counted by hemocytometer at 6, 12, and 24 hours. Statistical analysis was done using two-tailed Student's t-Test.

Figure 3:
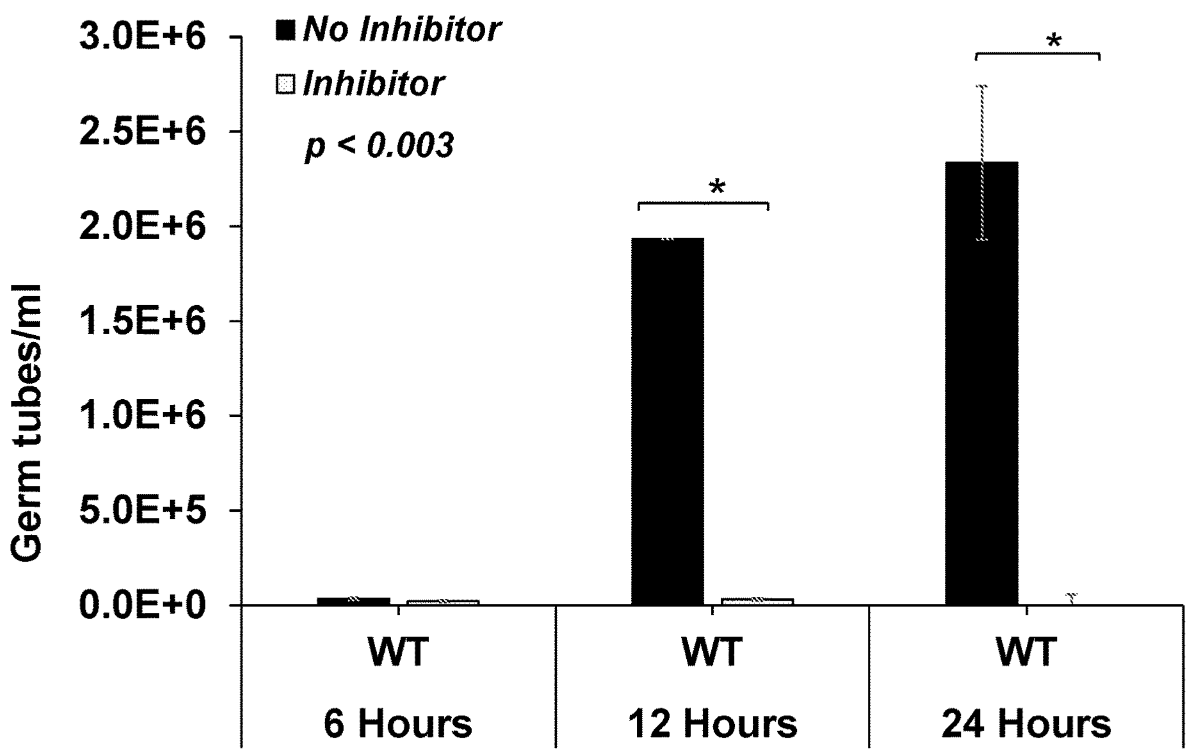
FIG. 3 is a representation of the effect of ManSIFG on hypha development of *Candida albicans*. The number of germ tubes/ml in the presence or absence of ManSIFg are shown at various times of exposure.

Formation of germ tubes in *C. albicans* wild type was inhibited by ManSIFG (62.5 µg/ml) significantly at 12 and 24 hours as compared to control cultures, which had normal germ tube formation (FIG. 3). This is a significant finding in that ManSIFG may be effective as an antifungal agent by inhibiting virulence pathogenesis of invasive mucosal candidiasis via hypha formation.

Combination of ManSIFG and Calcium Chloride Results in an Increased Antifungal Effect Calcium chloride ($CaCl_2$)) has been shown to activate the Ca-calcineurin signaling pathway in *C. albicans*. This signaling pathway is considered to regulate synthesis of chitin, an important carbohydrate which is part of the cell wall and septum, which is formed during cell division. *C. albicans* strain SC5314 (wild type) was cultured from frozen stock in Yeast Nitrogen Base media (YNB) with 2% glucose and grown overnight at 30° C. with shaking at 225 rpm. Cell concentration was determined by hemocytometer. A 5M stock solution of $CaCl_2$) made from Calcium chloride dihydrate ($CaCl_2$)-$2H_2O$) powder and distilled water and sterilized with a 0.22 um syringe filter. The overnight culture was used to inoculate fresh YNB supplemented with or without 0.2M $CaCl_2$) (from a 5M stock solution*) with a starting cell concentration of $5\times10^5$ cell s/ml in a total volume of 500 µl in small sterile tubes. ManSIFG (62.5 µg/ml) was added to test cultures but not to control cultures. The experiment was done in triplicates. The culture tubes were placed on a nutator inside a 30° C. incubator and grown for 24 hours. Time points were taken at 6, 12, and 24 hours. Cell concentration was monitored by hemocytometer at 6, 12, and 24-hour time points. Statistical analysis was done using two-tailed Student's t-Test.

Figure 4:
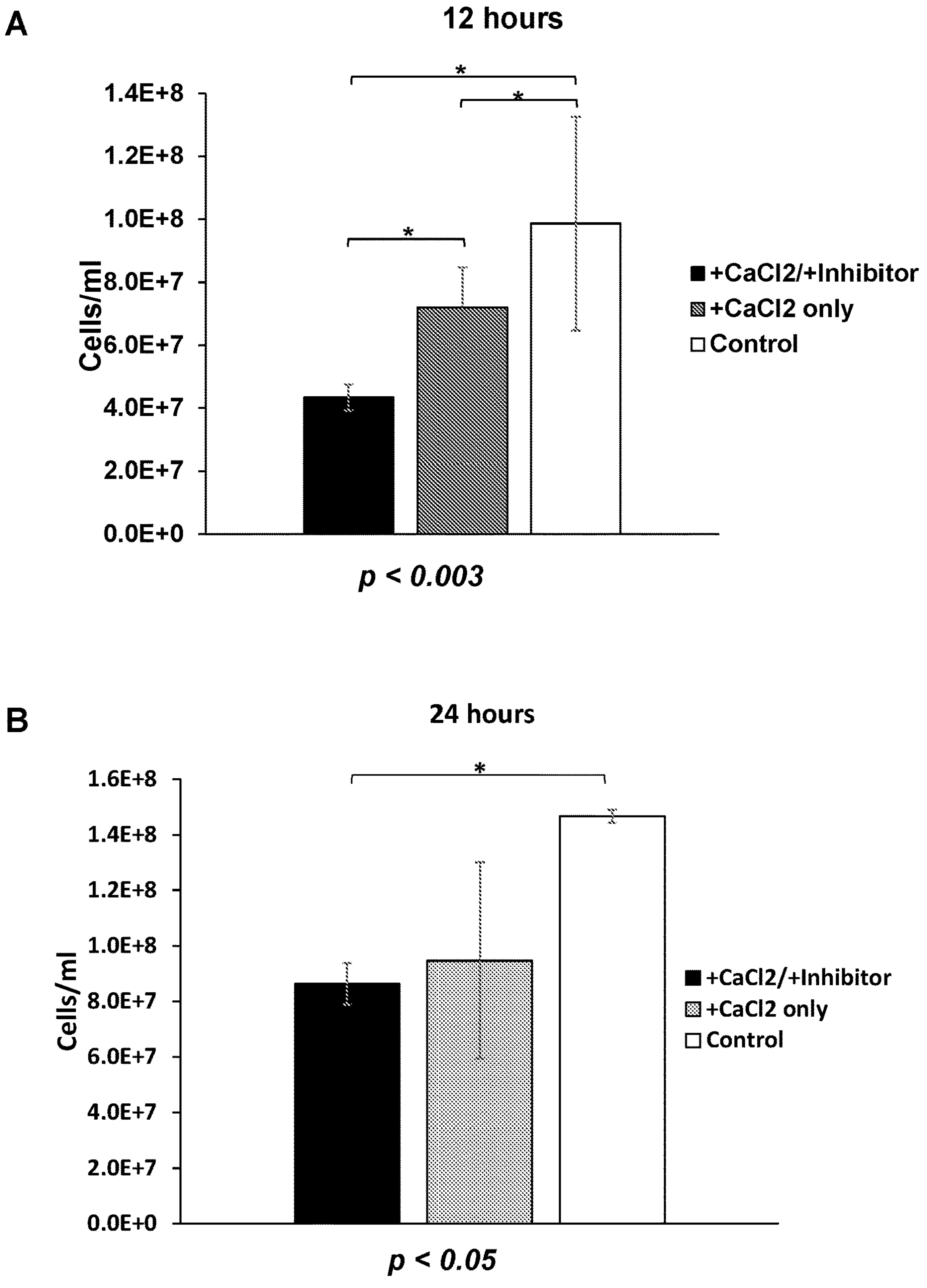
FIG. 4 is a representation of the effect of ManSIFG and $CaCl_2$) on the growth of *C. albicans* cells for (A) 12 hours and (B) 24 hours.

Data indicate that 0.2M $CaCl_2$ was able to significantly inhibit the growth of *C. albicans* both at 12 hours (FIG. 4A) and 24 hours (FIG. 4B) as compared to control cultures. Additionally, growth of *C. albicans* wild type was significantly inhibited by a combination of ManSIFG and $CaCl_2$) significantly at 12 hours (FIG. 4A) and 24 hours (FIG. 4B) as compared to control cultures. However, the inhibition of growth was more significant for ManSIFG and $CaCl_2$) combination as compared to $CaCl_2$) especially at 12 hours (FIG. 4A). At 24 hours there was no significant difference between ManSIFG and $CaCl_2$) combination as compared to $CaCl_2$) possibly due to the waning effect of the inhibitor due to processing (FIG. 4B). These data indicate that $CaCl_2$) increases the inhibitory effect of ManSIFG resulting in a potent combination therapeutic effect.

D-Mannose does not have any Antifungal Effect

Figure 5:
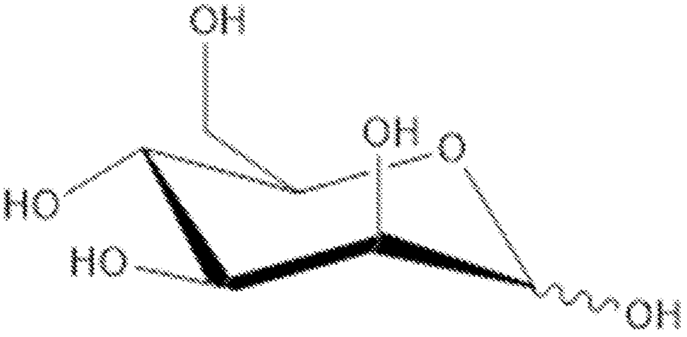
FIG. 5 is (A) a representation of the structure of the monosaccharide D-mannose and (B) a chart showing the effect of D-mannose on the growth of *C. albicans*.
Figure 5:
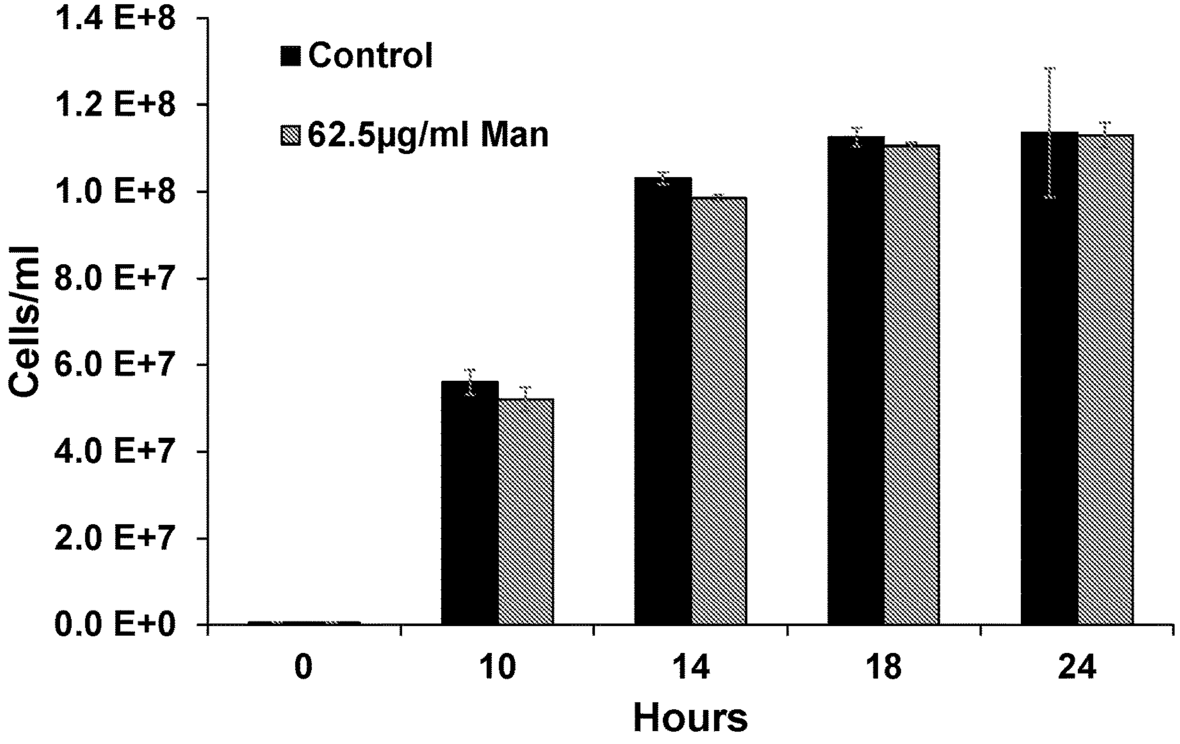

ManSIFG is a mannose disaccharide analog and has an antifungal effect. So we suspected if D-Mannose (FIG. 5A), which is a mannose monosaccharide, has an antifungal effect as well. The wildtype *C. albicans* strain SC5314 was cultured from frozen stock in Yeast Nitrogen Base (YNB) media with 2% glucose and grown overnight at 30° C. with shaking at 225 rpm as described previously. Cell concentration of the overnight culture was determined by hemocytometer. This was used to inoculate fresh cultures with a final starting concentration of $5\times10^5$ cells/ml in fresh YNB contain either no treatment (control) or 62.5 µg/ml of D-Mannose. The cultures were run in duplicates and incubated at 30° C. on a nutator. Cell concentration was analyzed by counting on hemocytometer at 10, 14, 18, and 24-hour time points. Results are shown in FIG. 5B. Statistical analysis was done using two-tailed Student's t-Test.

Growth of *C. albicans* wild type was not inhibited by D-Mannose (62.5 μg/ml) as compared to control cultures (FIG. 2). This lack of antifungal effect of D-Mannose demonstrates that ManSIFG has a unique structure and function that is highly effective at inhibiting the growth of *C. albicans* and other *Candida* species and other fugal genuses.

Example 2

This example provides further illustration of the effects of ManSIFG against *Candida* cells.

Figure 6:
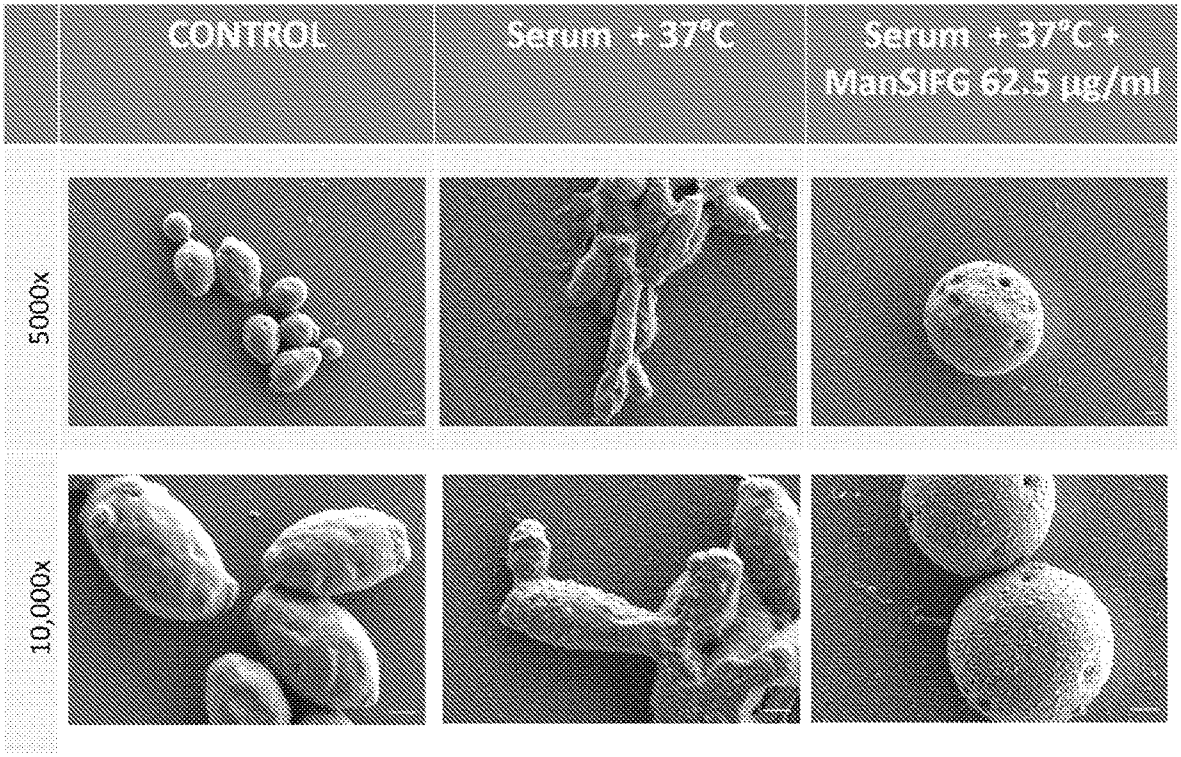
FIG. 6 is a representation of SEM images for *C. albicans* in control, serum, and serum containing ManSIFG at the indicated concentrations. Images are seen at 5000× and 10,000×.

ManSIFG inhibits hyphal formation and disrupts cell wall formation in *Candida albicans*. The *C. albicans* strain SC5314 (wild type) was cultured from frozen stock in Yeast Nitrogen Base (YNB) media with 2% glucose and grown overnight at 30° C. with shaking at 225 rpm. Cell concentration was determined by hemocytometer. The overnight culture was used to inoculate fresh YNB supplemented with or without 20% Fetal Bovine Serum (FBS) with a starting cell concentration of $5\times10^5$ cells/ml in a total volume of 500 μl in small sterile tubes, with or without 62.5 μg/ml ManSIFG. The experiment was done in triplicate. The culture tubes were placed on a nutator inside a 37° C. incubator and grown for 24 hours. The cultures were then transferred to 6-well polystyrene plates where the cells were allowed to settle for 90 min. at 37° C. on Fetal Bovine Serum (FBS, Seradigm) coated glass squares. The cells were fixed with cold 2.5% glutaraldehyde (Electron Microscopy Sciences, PA) in 1×PBS at 4° C. for 20 minutes. 1×PBS was added to wash the cells and left on for 10 minutes. The cells were dehydrated with a series of ethanol washes lasting 5 minutes each including 30, 50, 70, and 90% ethanol v/v in water with two final washes of 100% ethanol. The cells were not allowed to dry out until the final drying step with the chemical drying agent, hexamethyldisilazane (HMDS) (Acros Organics, Fisher Scientific, ON), which was left on for 5 minutes and then removed. The cells were then allowed to air dry completely. The samples were coated with evaporated carbon at high vacuum (Denton 502 Evaporator). SEM images were acquired with a Hitachi SU70 FESEM at 2.0 KeV using the lower detector and no tilt. Scanning electron microscopy (SEM) analysis of hyphal development shows that control cultures are able to develop into filamentous structures or hyphae in the presence of serum at 37° C. However, the ManSIFG treated group has complete inhibition of hyphal growth (FIG. 6). Additionally, the cells show disruption of the cell wall in the form of pores in the cell wall (FIG. 6). This clearly indicates the fungicidal effects of ManSIFG in *C. albicans.*

ManSIFG MIC analysis for *Candida albicans* and effects of CaCl2. A checkerboard synergy assay was used to test ManSIFG and $CaCl_2$) each by themselves and in various combinations of each other. Drug concentrations to be tested were prepared 4× concentrated and dispensed into a sterile 96-well culture plate. 25 ul of each ManSIFG dilution was dispensed in each column, such that concentrations increased along the x-axis of the plate. 25 ul of each CaCl2 dilution was dispensed in each row, such that concentrations increased along the y-axis of the plate. The *C. albicans* wild type strain (SC5314) was cultured from frozen stock in Yeast Peptone Dextrose (YPD) and grown overnight at 30° C. with shaking at 225 rpm. Cell concentration was determined by hemocytometer and used to adjust the inoculum to $2\times10^3$ cells/ml in fresh YPD, which is 2× the desired final concentration. 50 ul of the inoculum was added to each well for a final culture volume of 100 ul. The final cell concentration was $1\times10^3$ cells/ml. The plate was sealed with plastic film and placed in a BioTek Synergy HT plate reader for 24 hours at 37° C. At each time point, the plate was shaken for 10 seconds prior to each OD600 reading.

Figure 7:
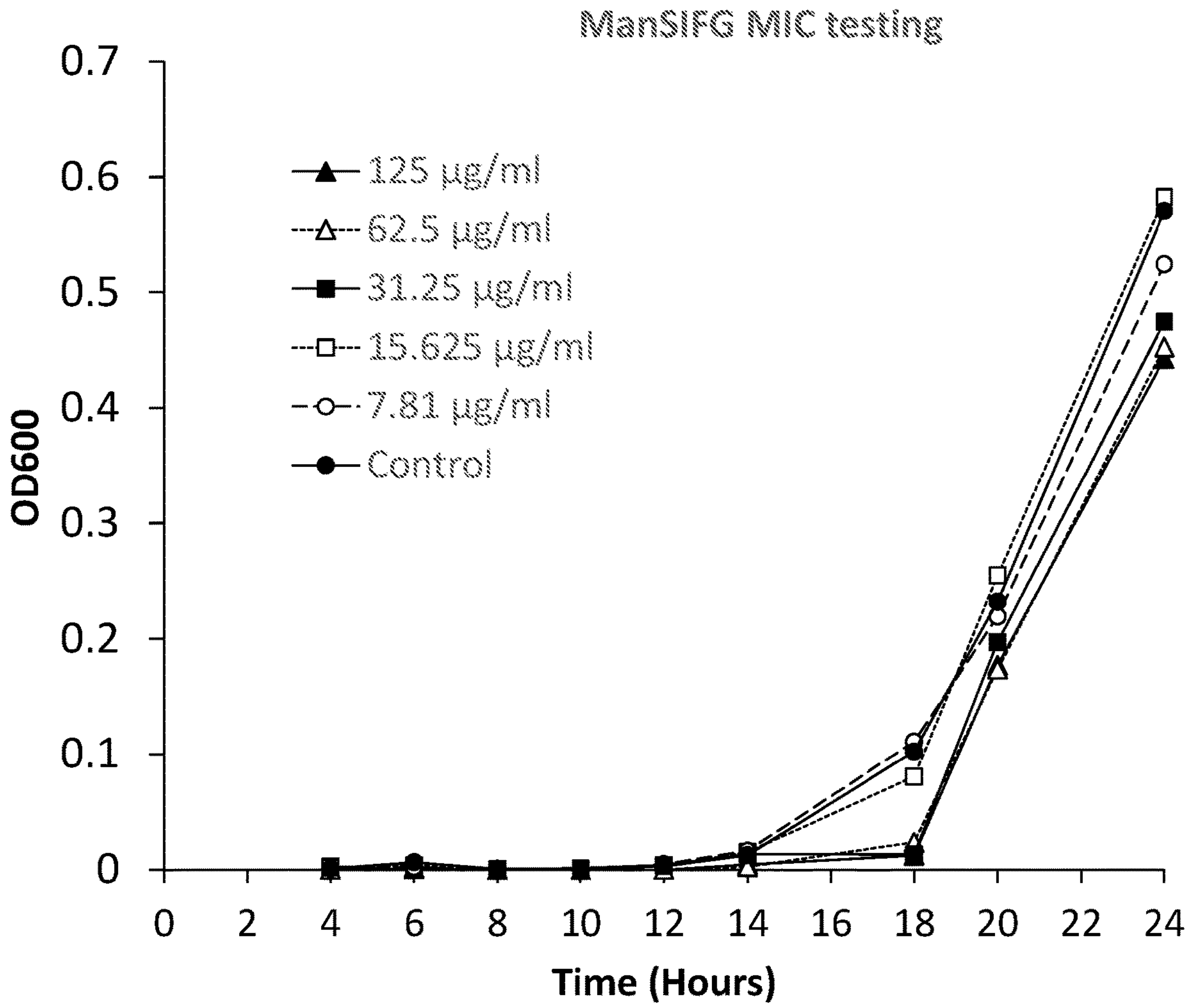
FIG. 7 shows MIC analysis for *C. albicans*. OD600 is shown as a function of time of growth for the indicated concentrations of ManSIGF.
Figure 8:
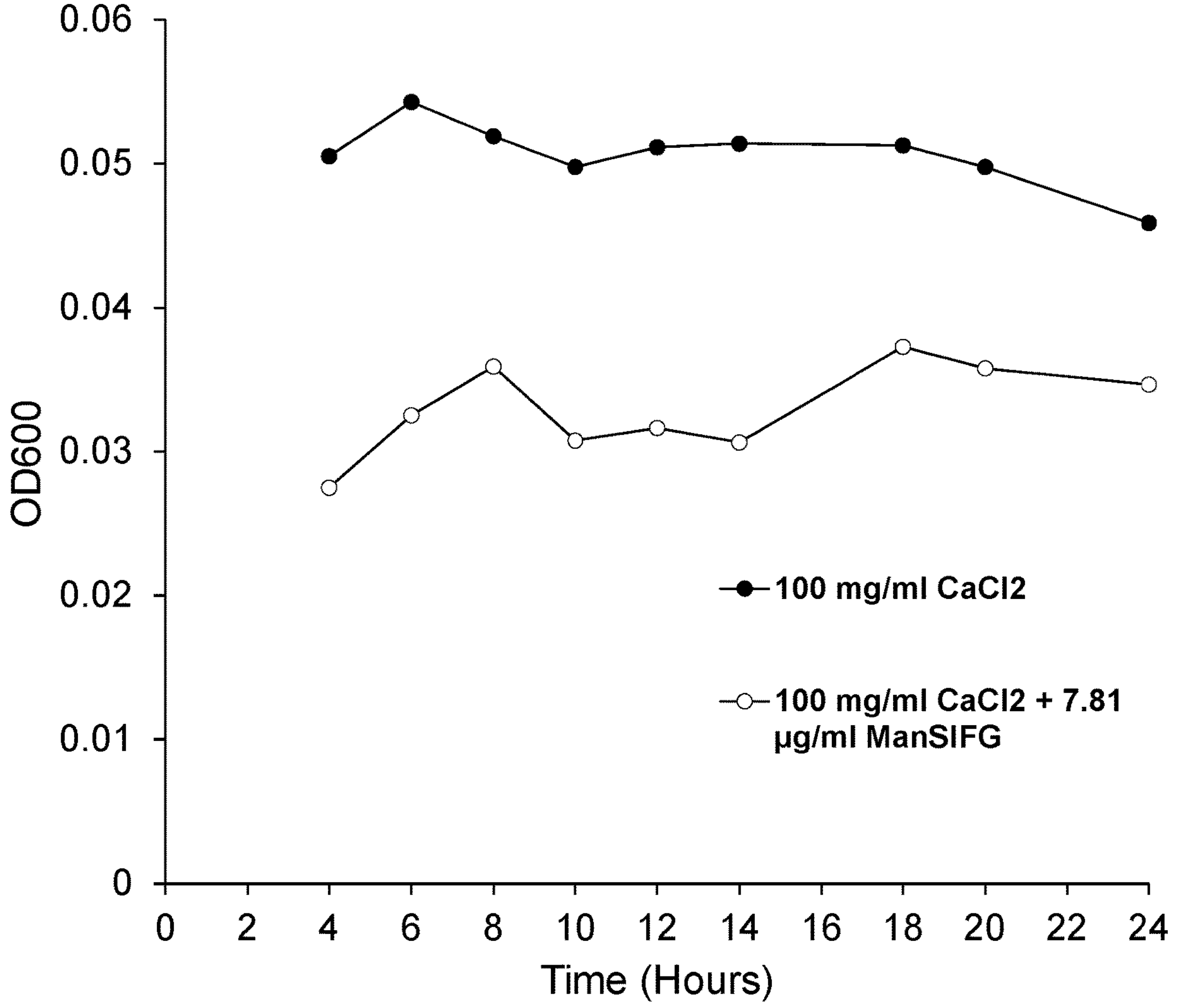
FIG. 8 is a representation of the effect of $CaCl_2$) on the antifungal activity of ManSIFG. OD600 is shown as a function of time for *C. albicans* cells in $CaCl_2$) alone or with ManSIFG. Closed circles are 100 mg/ml CaCl2, and open circles are 100 mg/ml CaCl2 plus 7.81 μg/ml ManSIFG.
Figure 9:
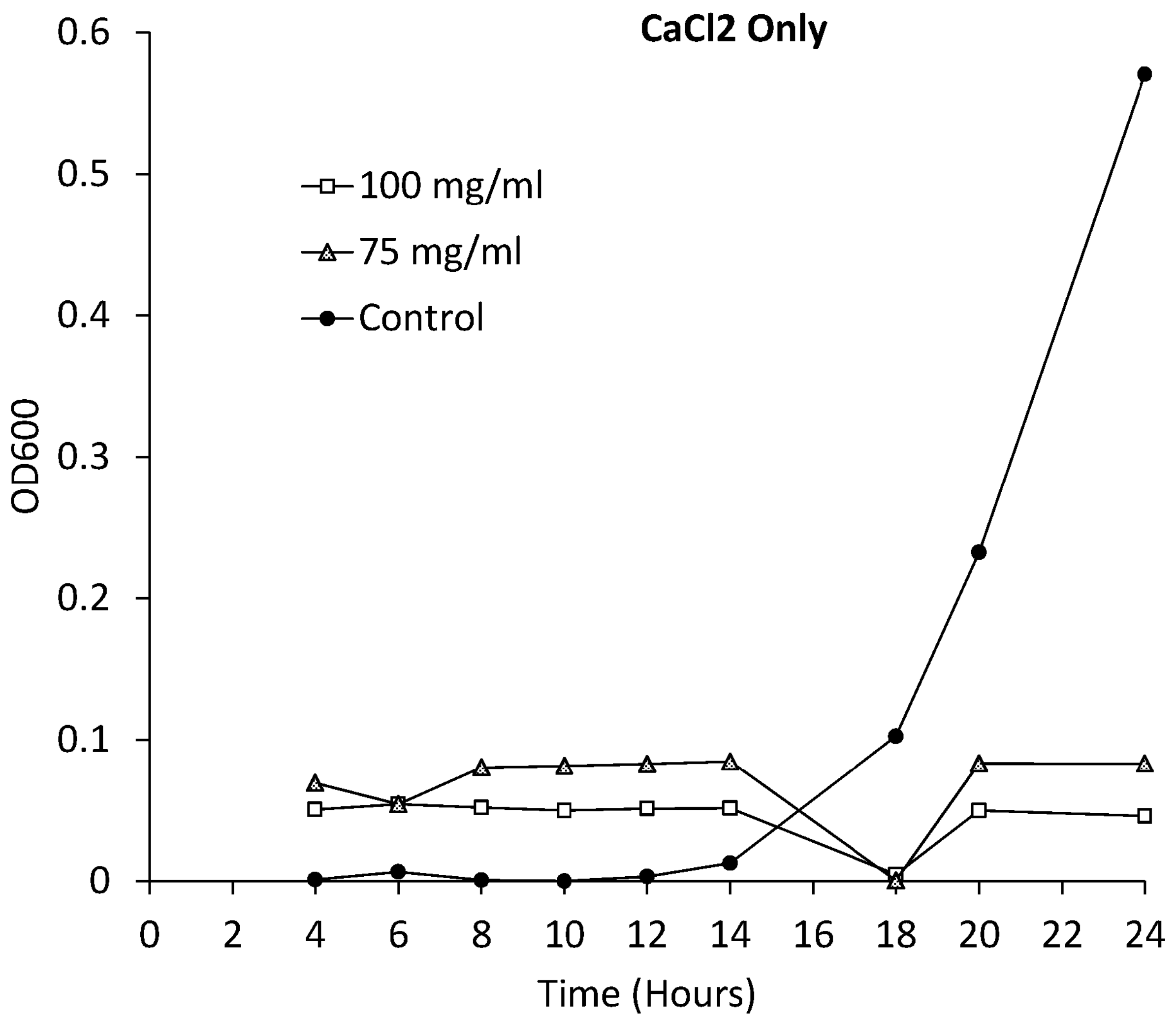
FIG. 9 shows the effect of $CaCl_2$) on the growth of *C. albicans*. MIC analysis is shown for the indicated concentrations of $CaCl_2$).

Results are shown in FIGS. 7-9. FIG. 7 shows the MIC value for ManSIFG ranges between 31.25 μg/ml and 62.5 μg/ml. FIG. 8 shows that the addition of $CaCl_2$ improves the antifungal activity of ManSIFG at low concentrations (7.81 μg/ml). Thus, $CaCl_2$) may have an additive effect on ManSIFG. FIG. 9 shows that $CaCl_2$) by itself has an antifungal effect. However, the concentrations of $CaCl_2$) are very high and may not be in the therapeutic range for treating invasive candidiasis but may still be useful for treating mucosal infections by topical application.

Figure 10:
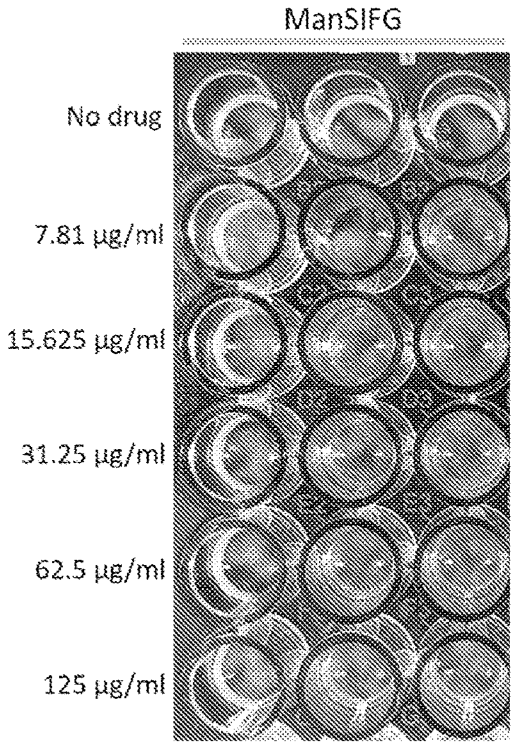
FIG. 10 shows the effect of ManSIFG on toe nail fungus *Trychophoton rubrum.*
Figure 11:
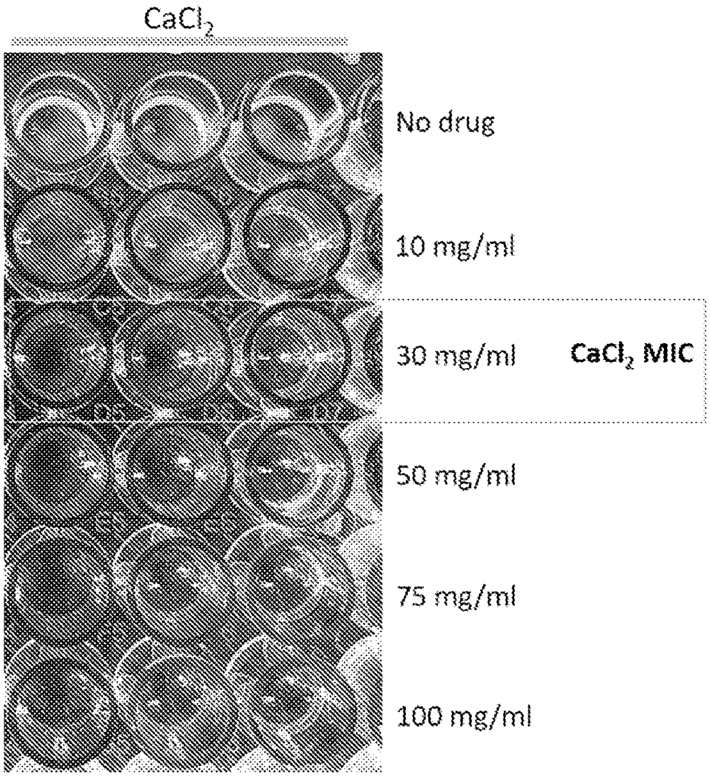
FIG. 11 shows the MIC analysis for the effect of $CaCl_2$) on toe nail fungus *Trychophoton rubrum.*

Effect ManSIFG on other fungal cells. *Trichophyton rubrum* is the fungal pathogen that causes onychomycosis or toe nail fungus. MIC testing was performed using ManSIFG and $CaCl_2$) for *Trychophyton rubrum* (ATCC-MYA-4607). Drug concentrations to be tested were prepared 2× concentrated and 50 ul per well for each was dispensed into a sterile 96-well culture plate. The experiment was performed in triplicates. Fresh conidia were collected, from 7-day cultures grown on Sabouraud Dextrose Agar (SDA), using 5 ml of sterile 0.9% NaCl+0.1% Tween20. Conidia concentration was determined by hemocytometer and used to adjust the inoculum to $2\times10^3$ cells/ml in fresh Sabouroud Dextrose Broth (SDB), which is 2× of the desired final concentration. A 50 ul inoculum was added to each well for a final culture volume of 100 ul. The final cell concentration was $1\times10^3$ cells/ml. The plate was cultured for 6 days at 25° C. and then imaged using an iPhone camera. Results are shown in FIGS. 10 and 11. FIG. 10 shows that ManSIFG was tested at various concentrations against the toe nail fungus, *Trychophoton rubrum*, and was found to show no inhibitory effect. At these concentrations, ManSIFG does not have antifungal activity against *T. rubrum*. FIG. 11 shows that $CaCl_2$ was tested at various concentrations against the toe nail fungus, *Trychophoton rubrum*, and was found to have a MIC between 20 and 30 mg/ml after 5 days of growth. At this MIC $CaCl_2$ may be used for topical application for treating onychomycosis.

Figure 12:
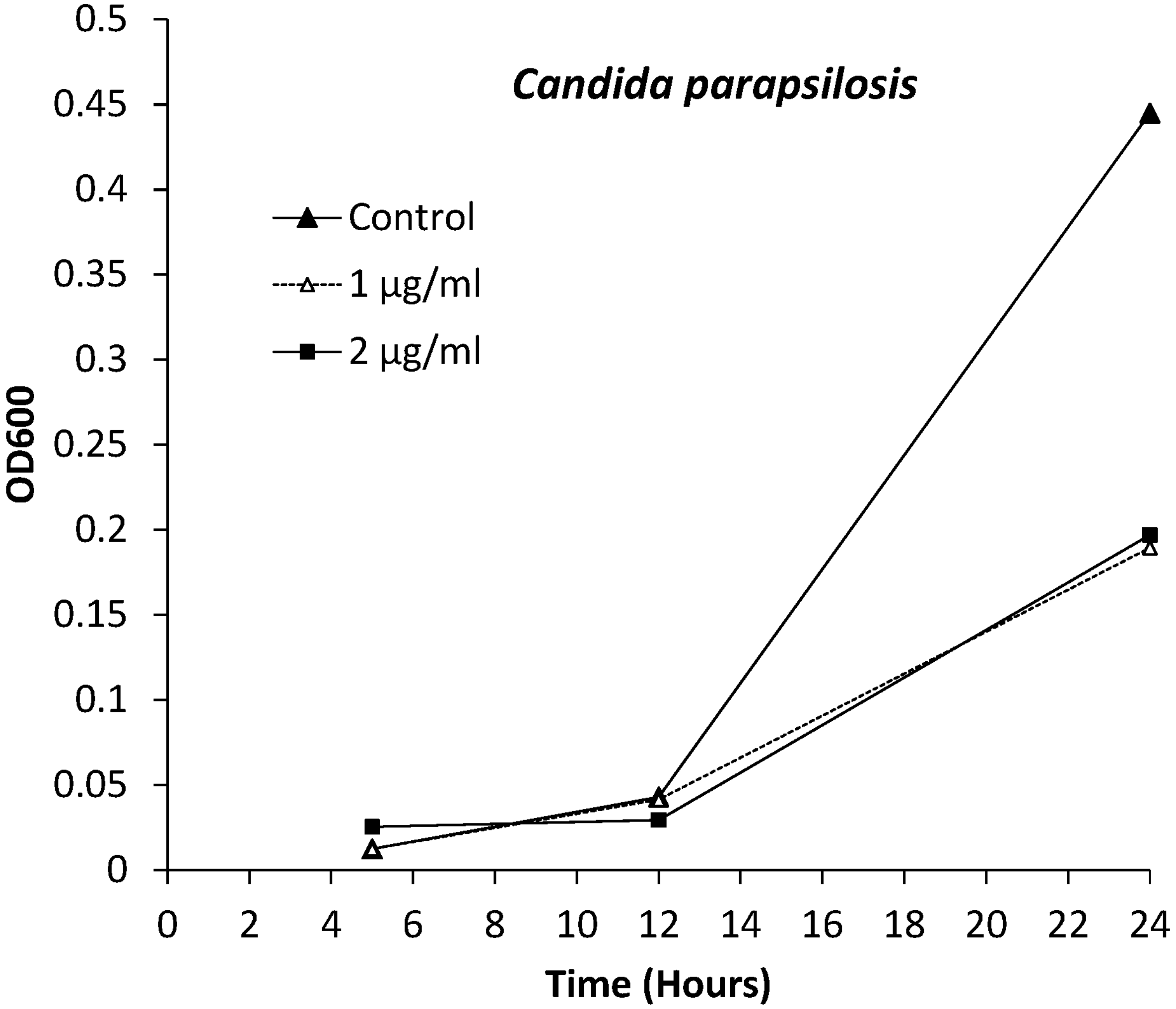
FIG. 12 shows the antifungal activity of ManSIFG against *C. parapsilosis.*
Figure 13:
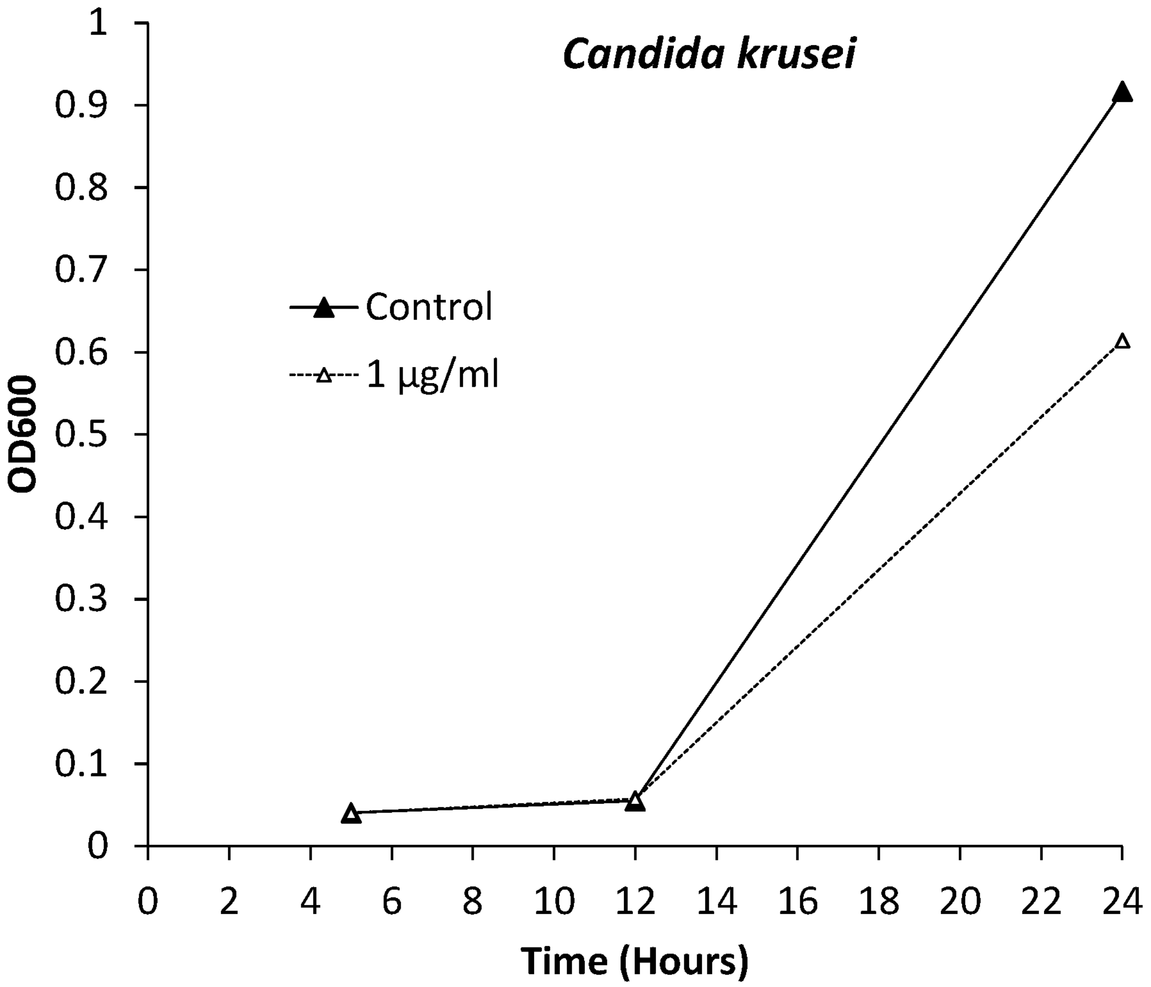
FIG. 13 shows the antifungal activity of ManSIFG against *C. krusei.*
Figure 14:
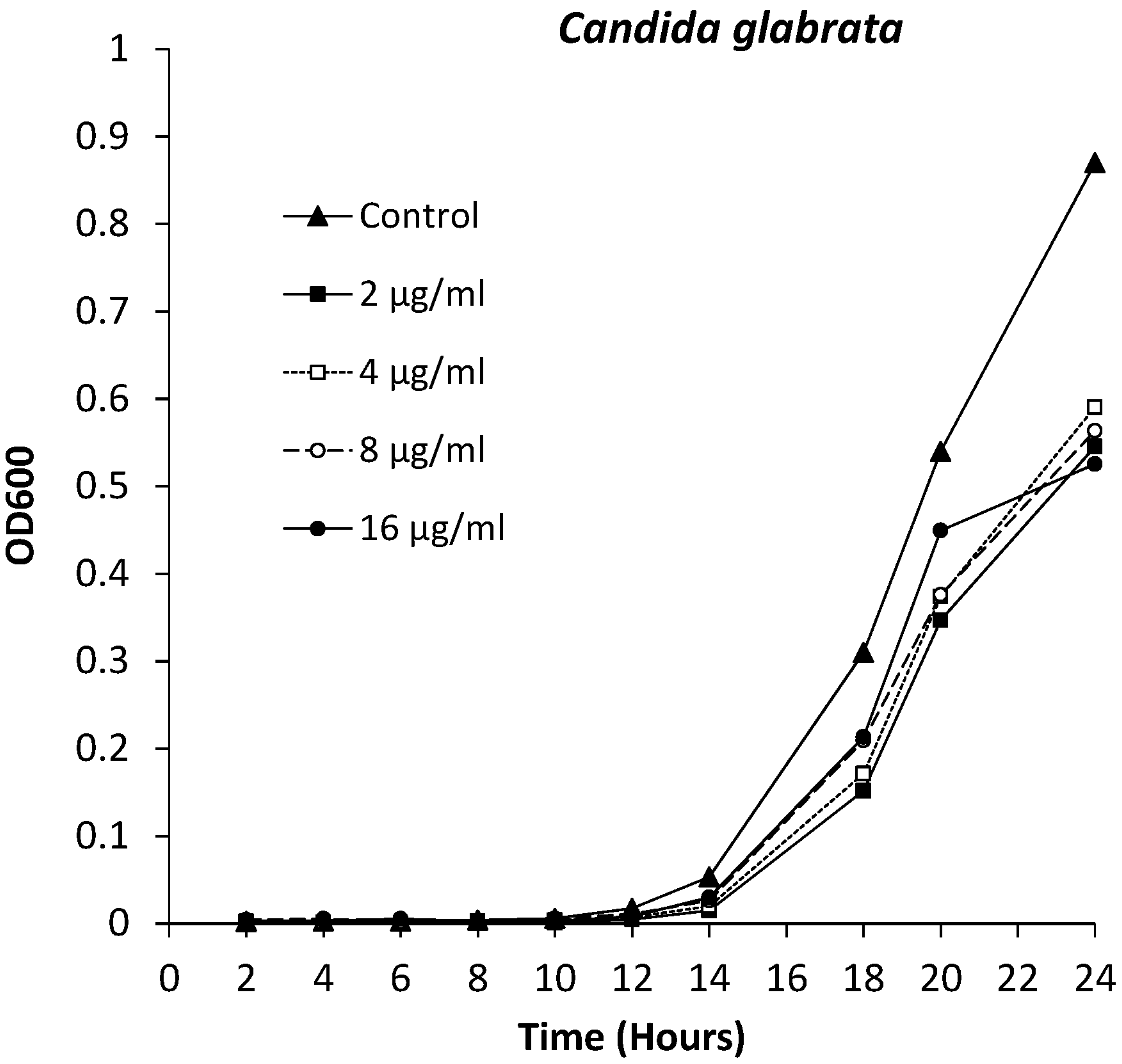
FIG. 14 shows the antifungal activity of ManSIFG against *C. glabrata.*
Figure 15:
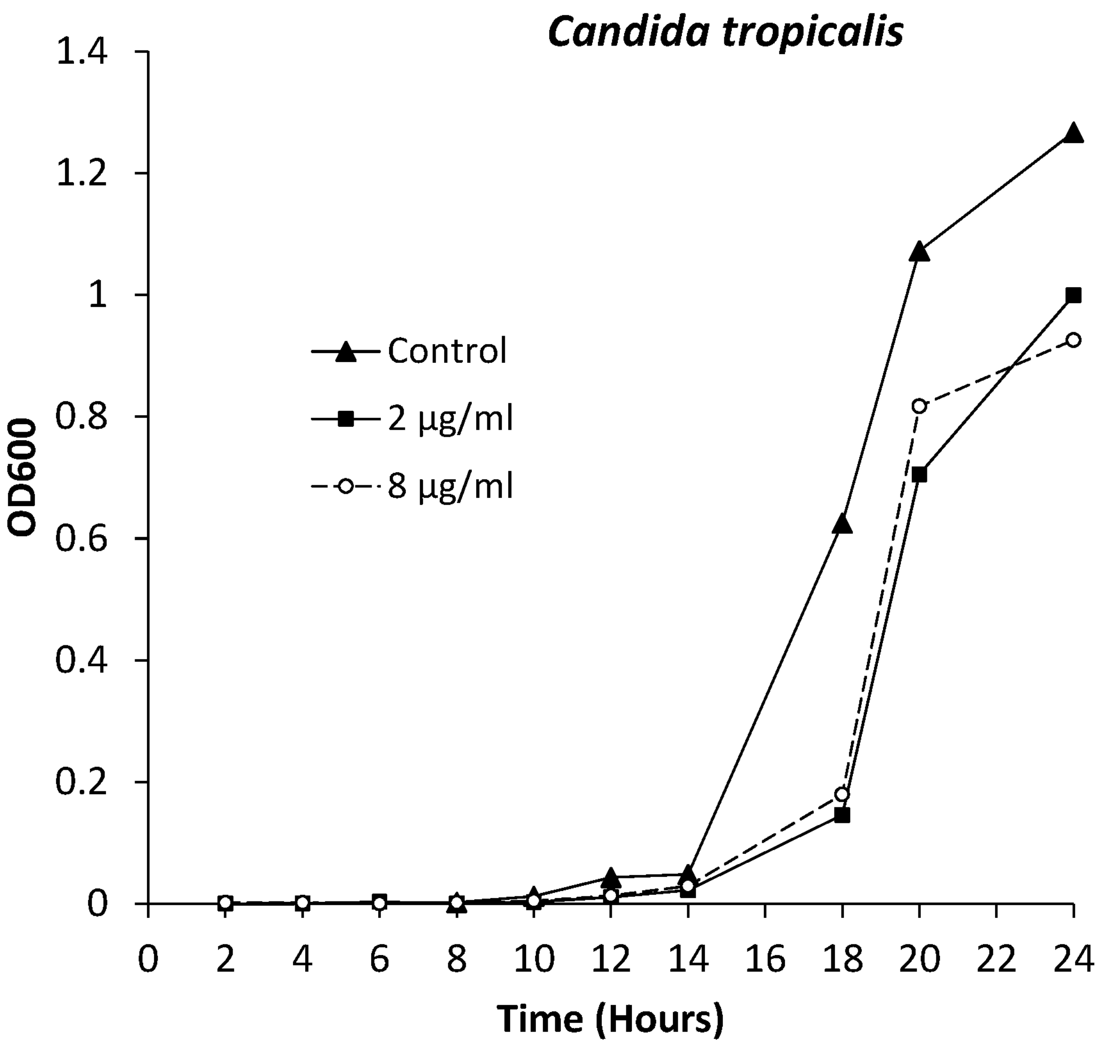
FIG. 15 shows the antifungal activity of ManSIFG against *C. tropicalis.*

Effect of ManSIFG on additional *Candida* species. Other *Candida* species were tested. *Candida parapsilosis* (ATCC-22019) wild type strain was used. Methods are same as described above. For *Candida krusei*, (ATCC-6258) wild type strain was used. For *Candida glabrata* (ATCC-2001) wild type strain was used, and for *Candida tropicalis* (ATCC-750) wild type strain was used. As shown in FIG. 12, ManSIFG has antifungal activity against *Candida parapsilosis* at very low concentrations. FIG. 13 shows that ManSIFG has antifungal activity against *Candida krucei* even at very low concentrations. FIG. 14 shows that ManSIFG has antifungal activity against *Candida glabrata*, and FIG. 15 shows that ManSIFG has antifungal activity against *Candida tropicalis*. These additional *Candida* species are considered to have etiopathogenic role in invasive candidiasis along with *Candida albicans.*

The invention has been described through some embodiments. Routine modifications to the embodiments and the disclosure will be apparent to those skilled in the art and such modifications are intended to be within the scope of the disclosure.

What is claimed is:

1. A composition comprising a compound having the following structure Formula I):

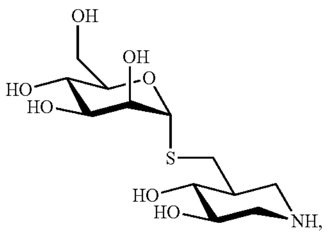

including α and β diastereomers and/or pharmaceutically acceptable salts thereof in a pharmaceutical carrier, wherein the compound is present at a concentration of 5 micrograms/mL to 31.25 micrograms/mL; and a calcium salt present at a concentration of 5 mg/mL to 120 mg/mL.

2. The composition of claim 1, wherein the calcium salt is calcium chloride, calcium phosphate, calcium carbonate, calcium acetate, calcium gluconate, calcium lactate, calcium gluceptate or calcium glycerophosphate.

3. The composition of claim 1, wherein the calcium salt is $CaCl_2$.

4. The composition of claim 1, wherein the compound of formula I is the only disaccharide present and wherein the composition is free of monosaccharides or trisaccharides.

5. The composition of claim 1, wherein the composition is suitable for topical application.

6. The composition of claim 1, wherein the compound is present at a concentration of 5 micrograms/ml to 25 micrograms/ml.

7. The composition of claim 1, wherein the composition is present as an ointment, paste, gel, liquid, solid, or aerosolized.

8. A method of treating a fungal infection comprising administering to an individual in need of treatment, or contacting an infected area of the individual with, a composition of claim 1, wherein treating consists of alleviation of acute or chronic signs and/or malfunctions associated with fungal infection and the fungal infection is associated with or caused by *Candida, Aspergillus*, or *Trychophoton.*

9. The method of claim 8, where administration comprises contacting an infected area of the individual.

10. The method of claim 9, wherein the compound is administered at a dosage of 0.05 to about 100 mg/kg of body weight per day.

11. The method of claim 8, wherein the infection is caused by one or more of *Candida albicans, Candida guilliermondii, Candida glabrata, Candidia parapsilois, Candidia apicola, Candida tropicalis, Candida lustaniae, Candida krusei, Trychophoton rubrum, Trychophoton mentagrophytes, Trychophoton verrucosum*, and *Trychophoton tonsurans.*

* * * * *